United States Patent [19]

Ohata et al.

[11] 3,934,139

[45] Jan. 20, 1976

[54] APPARATUS FOR MEASURING CALORIFIC POWER OF HYDROCARBON COMPOUNDS

[75] Inventors: Shuichi Ohata; Yoji Takeuchi; Takeshi Ishiguro, all of Musashino, Japan

[73] Assignee: Yokogawa Electric Works, Ltd., Tokyo, Japan

[22] Filed: Sept. 19, 1973

[21] Appl. No.: 398,683

[30] Foreign Application Priority Data

Sept. 29, 1972 Japan.............................. 47-98360

[52] U.S. Cl. ............... 250/308; 250/356; 250/372; 250/383
[51] Int. Cl.² .......................................... G01N 23/00
[58] Field of Search ........... 250/460, 356, 372, 373, 250/383, 308; 324/33

[56] References Cited
UNITED STATES PATENTS

| | | | |
|---|---|---|---|
| 2,706,789 | 4/1955 | Hughes | 250/383 |
| 2,883,542 | 4/1959 | Jacobs | 250/383 |
| 2,899,555 | 8/1959 | Fries | 250/383 |
| 2,937,275 | 5/1960 | Thourson et al. | 250/383 |
| 3,254,214 | 5/1966 | Bennett | 250/383 |

*Primary Examiner*—Harold A. Dixon
*Attorney, Agent, or Firm*—Parmelee, Johnson & Bollinger

[57] ABSTRACT

An apparatus for continuously measuring with safety and high accuracy the calorific power of a sample containing hydrocarbon compounds and sulfur, such as crude oil and petroleum products. The apparatus supplies two energy levels of radioactive rays to be absorbed by the sample, a first supply of the radioactive rays having an energy level at which the mass absorption coefficient of carbon differs from that of hydrogen, and a second supply of rays having an energy level at which the mass absorption coefficient of carbon is approximately equal to that of hydrogen. The first rays yield a signal varying with the concentrations of hydrogen, carbon and sulfur in the sample, while the second rays yield a signal varying with the concentration of sulfur in the sample. The signals are density compensated, and mathematically correlated according to a predetermined arithmetic formula to determine the calorific power of the sample hydrocarbon compound.

11 Claims, 3 Drawing Figures

APPARATUS FOR MEASURING CALORIFIC POWER OF HYDROCARBON COMPOUNDS

BACKGROUND OF THE INVENTION

1. Field of the Invention

The present invention relates to apparatus for measuring the calorific power of hydrocarbon compounds such as crude oil and petroleum products.

2. Description of the Prior Art

Calorific power is an important measure to determine the quality of crude oil and petroleum products. For example, in a power plant where a large amount of petroleum fuel is consumed, the calorific power of the fuel used is a significant factor in determining the cost of the power generated. This circumstance has called for the most precise calorific power measurement or analysis, which, however, has been dependent upon manual processes even in a highly automated power plant. One well-known calorific power measuring method uses an adiabatic bomb wherein a given amount of petroleum is burned to measure the calorific power. In this method the calorific power can be measured directly, but at the sacrifice of time taken for measuring preparations and procedures. Furthermore, this method requires the use of a precision thermometer to detect very small temperature variations, and measuring accuracy is significantly affected by the manner of measurement and the instruments used.

Another method of measuring the calorific power of a hydrocarbon compound uses neutrons and proceeds on the principle that the hydrogen atomic nucleus in crude oil has the prime decelerating effect on the neutron. The density of the hydrocarbon atomic nuclei is measured through measurement of thermal neutrons generated by the deceleration and the calorific power is approximately measured by the use of a nearly constant carbon-to-hydrogen weight ratio. This method permits continuous calorific power measurement without the necessity of extracting a sample of the process hydrocarbon compound, with the result that labor is saved and the measuring accuracy is independent of a technician's personal skill. However, because this method is primarily intended to measure the density of hydrogen atomic nuclei, some measuring error is inevitable if a third substance such as sulfur is present in the process hydrocarbon compound, which leads to changes in the carbon-to-hydrogen concentration ratio. Furthermore, the neutron detecting instrument used in this method is generally of low stability and often causes measuring error. In addition, when exposed to neutrons, a substance is caused to radiate gamma rays which are dangerous to man and can give rise to measuring error.

SUMMARY OF THE INVENTION

The principal object of the present invention is to provide an apparatus capable of continuously measuring with safety and high accuracy the calorific power of hydrocarbon compounds such as crude oil and petroleum products.

In one aspect of the invention gamma rays or X-rays, at an energy level for which the mass absorption coefficient of carbon differs from that of hydrogen, are applied to a sample hydrocarbon compound, the absorption rate is detected, and a signal varying with the carbon-to-hydrogen concentration ratio, given in terms of the absorption rate detection signal, is compensated with respect to density by a signal related to the measured density of the sample and then computed or modified according to a given formula by a computing means to determine the calorific power of the sample hydrocarbon compound.

In a second aspect of the invention the apparatus further comprises a sulfur concentration measuring means, and a sulfur concentration signal and said density-compensated carbon-to-hydrogen concentration ratio signal applied to the computing means and computed according to a given correlating formula to measure the calorific power of the sample containing sulfur with high accuracy.

In a third aspect of the invention, a measuring apparatus is provided with a gamma ray source and a target which, when irradiated with gamma rays, emits flourescent X-rays, in order to provide both gamma rays or flourescent X-rays at an energy level on which the mass absorption coefficient of carbon differs from that of hydrogen, and flourescent X-rays at an energy level which the two mass absorption coefficients are the same. The gamma rays or flourescent X-rays having different energy levels are applied to a sample hydrocarbon compound, and a detector means comprising one or separate detectors is used to generate both a signal varying with the concentrations of carbon, hydrogen and sulfur, and a signal varying with the sulfur concentration independently of the concentrations of carbon and hydrogen.

Other objects, aspects and advantages of the invention will be pointed out in, or apparent from, the following detailed description, taken in conjunction with the following drawings.

DESCRIPTION OF THE PREFERRED EMBODIMENTS

Figure 1:
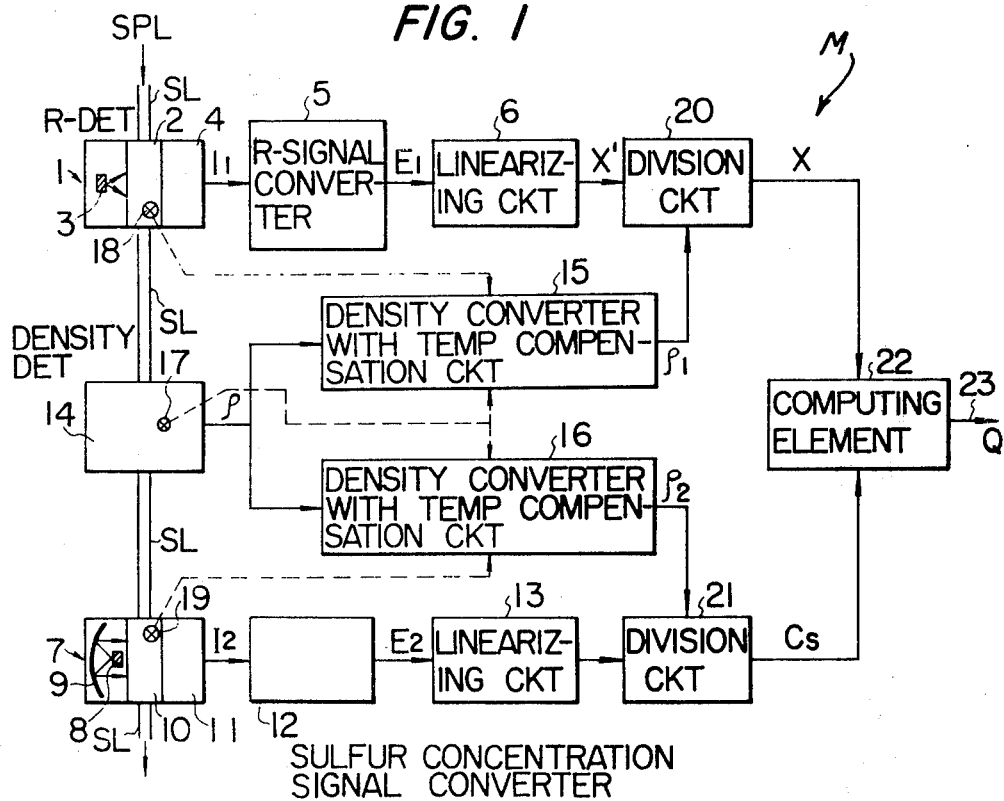
FIG. 1 is a block diagram showing an apparatus arranged for measuring calorific power in accordance with the present invention.

Before describing the specific measuring apparatus M illustrated in FIG. 1, it is helpful to supply a parallel mathematical analysis and explanation of the operations which the measuring apparatus undertakes in obtaining a measurement.

Assume that gamma rays or X-rays, at an energy level of, for example, 60 keV, for which the mass absorption coefficient of carbon differs from that of hydrogen, are applied to a sample hydrocarbon compound and the absorption rate thereof is detected by a suitable detector such as an ionization chamber. Then the output current $I_1$ of the ionization chamber is given as $$I_1 = I_{01} e^{-\rho_1 t_1 (\mu_S c_S + \mu_H c_H + \mu_C c_C)} \quad (1)$$

where $I_{01}$: the output current of the ionization chamber without the sample $\rho_1$: the density of the sample $t_1$: the effective length of the sample cell $\mu_S, \mu_H, \mu_C$: the mass absorption coefficients of sulfur, hydrogen, and carbon $C_2, C_H, C_C$: the concentrations of sulfur, hydrogen and carbon.

The relationship among $C_S$, $C_H$ and $C_C$ is:

$$C_S + C_H + C_C = 1 \quad (2)$$

The carbon-to-hydrogen concentration ratio R is $$\frac{C_c}{C_h} = R \tag{3}$$

Rearranging Eq. (1) in terms of R and $C_S$ according to Eqs. (2) and (3), $$I_1 = I_{01} \cdot \rho_1 \cdot t_1 \left\{ \mu_S \, {}^{C_S + (1 - C_S)} \, \frac{\mu_H + \mu_c R}{R + 1} \right\} \tag{4}$$

The calorific power Q of the sample is given as follows if the amount of impurity content is negligible.

$$Q = Q_S C_S + Q_H C_H + Q_C C_C \tag{5}$$

where $Q_S$, $Q_H$ and $Q_C$ stand for calorific powers per unit weight of sulfur, hydrogen and carbon.

The concentrations $C_H$ and $C_C$ of Eq. (5) may be replaced by R and $C_S$ by using Eqs. (2) and (3), $$Q = Q_S C_S + (1 - C_S) \frac{Q_H + Q_C R}{R + 1} \tag{6}$$

It is apparent that the exponential term in the braces of Eq. (4) is similar in form to Eq. (6) with respect to $C_S$ and R. If the output current $I_1$ of the ionization chamber given by Eq. (4) is linearized by a linearizing circuit such as a logarithmic amplifier, a signal X' as given by Eq. (7) is obtained.

$$X' = \rho_1 t_1 \left\{ \mu_S C_S + (1 - C_S) \frac{\mu_H + \mu_c R}{R + 1} \right\} \tag{7}$$

When the signal X' is divided by the density signal $\rho_1$ of the sample by using a divider and multiplied by a suitable factor, i.e. $1/t_1$, one obtains a signal X given as $$X = \mu_S C_S + (1 - C_S) \frac{\mu_H + \mu_c R}{R + 1} \tag{8}$$

By eliminating R from Eqs. (6) and (8), then Eq. (6) may be rewritten as expressed by Eq. (9) below.

$$Q = \left\{ \frac{Q_H - Q_c}{\mu H - \mu C} \right\} X + \left\{ Q_c - \frac{\mu C}{\mu H - \mu C}(Q_H - Q_c) \right\}$$

$$+ \left\{ Q_s - Q_c - \frac{\mu S - \mu C}{\mu H - \mu C}(Q_H - Q_c) \right\} C_S \tag{9}$$

In Eq. (9) the terms in braces are all constants. Therefore the calorific power Q (i.e., the total calorific power) of the sample can be measured when the sulfur concentration $C_S$ is found by a sulfur concentration measuring means, and the sulfur concentration signal $C_S$ and the signal X, which varies with sulfur concentration $C_S$ and with the carbon-to-hydrogen concentration ratio R as in Eq. (8), are computed or correlated according to Eq. (9) by using a suitable computing means.

If no sulfur is contained in the tested hydrocarbon compound or if sulfur is present therein but negligible in amount, the sulfur concentration signal is zero and no sulfur concentration measuring means is needed.

To satisfy Eq. (9), the condition $\mu_H \neq \mu_C$ must hold. This indicates that the calorific power of a hydrocarbon compound can be measured by the use of gamma rays or X-rays at an energy level on which the mass absorption coefficient of carbon differs from that of hydrogen.

Referring now to the specific measuring apparatus M shown in FIG. 1, the apparatus M includes a detector 1 (hereinafter referred to as an R-detector) capable of generating a signal which varies, as will be explained below, with the concentration ratio R of carbon to hydrogen, the concentraton $C_S$ of sulfur, and the density $\rho_1$ of a sample hydrocarbon compound SPL. The R-detector 1 comprises a sample cell 2 to which the sample SPL is continuously supplied through a supply line SL, a radiation source 3 generating gamma rays or X-rays at an energy level of, for example, 60 keV, for which the mass absorption coefficient of carbon differs from that of hydrogen, and a detector 4, for example, an ionization chamber, located next to the sample cell 2 opposite the radiation source 3, for detecting the gamma rays or X-rays transmitted through the sample in the sample cell 2. The output signal I1 from the ionization chamber 4 is supplied to an R-signal converter 5 for impedance-converting the output current I1 as well as for converting it into a constant level electric signal such as a voltage signal E1 of 1 to 5 V DC. The voltage signal E1 is applied to a linearizing circuit 6, such as a logarithmic amplifier for linearizing the output of the R-signal converter 5.

Measuring apparatus M further includes a sulfur concentration detector 7 capable of generating a signal I2 which varies not with the carbon-to-hydrogen concentration ratio R of the sample SPL but instead varies with its sulfur concentration $C_S$. The sulfur concentration detector 7 comprises a primary radiation source 8, such as $241_{Am}$ whose energy is 60 to 100 keV or an X-ray generator, a target 9 made, for example, of silver and tin in an area ratio of 50/50, or of indium, capable of generating flourescent X-rays whose energy is about 20 keV, or preferably 23 to 24.5 keV, and a radiation detector 11 such as an ionization chamber located next to sample cell 10 opposite the target 9. The sample cell 10 communicates with the sample cell 2 of R-detector 1 and is continuously supplied with the sample SPL. The output current of the ionization chamber 11 is applied to a sulfur concentration signal converter 12 for impedance-converting, as well as for converting it into a constant level voltage signal E2 such as 1 to 5 V DC. A linearizing circuit 13, such as a logarithmic amplifier, is provided for linearizing the output E2 of the sulfur concentration signal converter 12.

A density detector 14, such as a vibration type density meter, measures the density of the sample SPL by measuring the lateral free vibration of the pipe carrying the sample. This type of density meter is desirable because it can continuously measure density with high accuracy. The density detector 14 is located in the middle of the sample line SL which communicates between the R-detector 1 and the sulfur concentration detector 7 so that the density of the sample SPL flowing through the R-detector and the sulfur concentration detector can be measured as it exists at each such detector.

Density converters 15 and 16, each having a temperature compensation circuit, are responsive to (1) the temperature of the sample in the density detector 14 as detected by a resistance bulb 17, and either (2) the temperature of the sample flowing through the sample cell 2 of R-detector 1 as detected by a resistance bulb 18, or (3) the temperature of the sample flowing through the sample cell 10 of the sulfur concentration detector 7 as detected by a resistance bulb 19. Density converters 15 and 16 convert the density signal $p$ from detector 14 into reference temperature converted density signals $\rho_1$ and $\rho_2$ relating density as detected by detector 14 to the temperatures as sensed by bulbs 18 and 19 respectively in the R-detector 1 and sulfur concentration detector 7. A density signal $\rho_1$ for the sample at the R-detector and a density signal $\rho_2$ for the sample at the sulfur concentration detector are obtained.

The density signals $\rho_1$ and $\rho_2$ are applied to division circuits 20 and 21 for eliminating the density variables contained in the outputs of the linearizing circuits 6 and 13 and for generating both a linear signal X which varies with sulfur concentration $C_S$ and the ratio R irrespective of density changes, and a linear signal $C_S$ which varies with the sulfur concentration $C_S$. A computing element 22 receives the outputs X and $C_S$ of the division circuits 20 and 21, and computes or correlates them according to Eq. (9) to generate on output line 23 the signal Q representing the calorific power of the sample.

The measuring apparatus M of FIG. 1 operates in the following manner. Assume that the sample SPL is continuously introduced into the R-detector 1, density detector 14, and the sulfur concentration detector 7. Then the R-detector 1 generates a signal $I_1$ related to R as in Eq. (4). This signal $I_1$ is impedance converted into a 1 to 5 V DC signal $E_1$ by the R signal converter 5 and then logarithmically converted into a signal X' as in Eq. (7) by the linearizing circuit 6. The density signal output $p$ of the density detector 14 is converted with respect to a reference temperature and compensated with respect to the temperature at which R is detected, yielding the density signal $\rho_1$ at that detector. The signal X' is then divided by the density-compensated signal $\rho_1$ and multiplied by $1/t_1$ whereby a signal X related not to density but to $C_S$ and R as in Eq. (8) is obtained.

In the sulfur concentration detector 7, the target 9, when irradiated with gamma rays from the radiation source 8, emits flourescent X-rays of 23.5 keV energy. The ionization chamber 11 generates a current signal $I_2$ corresponding to the absorption rate of the flourescent X-rays transmitted through the sample in the cell 10. This signal $I_2$, not related to R, is given as $$I_2 = I_{o2}e^{-\rho_2 \, t_2 \{(\mu_S - \mu_{CH})C_S + \mu_{CH}\}} \quad (10)$$

where $I_{o2}$: the output current of the ionization chamber 11 when the sample cell 10 is empty $\rho_2$: the density of the sample when the sulfur concentration is measured $t_2$: the effective length of the sample cell 10

$\mu_{CH}$: the mass absorption coefficient of a hydrocarbon compound

The output signal $I_2$ of the detector 7 as in Eq. (10) is converted into a voltage signal $E_2$, for example, a DC 1 to 5 V signal after impedance conversion by the sulfur concentration signal converter 12. Then the signal $E_2$ is linearized through logarithmic conversion by the linearizing circuit 13 and supplied as an input to the division circuit 21. The division circuit 21 is supplied also with density signal $\rho_2$ which is the output of the density detector 14 after being converted according to a reference temperature and then compensated with respect to the temperature at which the sulfur concentration is detected. Division circuit 21, using this density signal $\rho_2$, in addition to other necessary arithmetic operations, eliminates the density $\rho_2$, the effective length $t_2$ of the sample cell 10, the current $I_{o2}$ of the ionization chamber when the sample cell 10 is empty, and the mass absorption coefficients $\mu_S$ and $\mu_{CH}$ of sulfur and hydrocarbon to obtain an output signal $C_S$ related only to the sulfur concentration $C_S$.

The output X of the division circuit 20 and the output $C_S$ of the division circuit 21 are supplied to the computing element 22 in which the two outputs X and $C_S$ are computed or correlated according to Eq. (9). The computed result, an electrical signal proportional to the calorific power Q of the sample, is available at the output terminal 23.

The following numbers set forth one concrete example wherein the calorific power Q of a hydrocarbon compound is determined by the use of gamma rays of 60 keV energy, at which $\mu_H = 0.37$ cm²/g, $\mu_C = 0.175$ cm²/g, and $\mu_S = 0.43$ cm²/g. Substituting $Q_H$ (33,888 kcal/kg), $Q_C$ (7,831 kcal/kg) and $Q_S$ (2,210 kcal/kg) for Eq. (8), $Q = 133625.64 X - 39693.13\, C_S - 15552.55$ kcal/kg When this hydrocarbon compound is petroleum where $R = 7$ and $C_S = 0.02$ (2%), then $X = 0.20448$. Substituting these values for Eq. (11), $Q = 10976.89$ kcal/kg In this example, if the calorific power is measured with a resolution $\Delta Q = 20$ kcal/kg (or about 0.2%), the resolution $\Delta X$ of X should be 0.015%, and the resolution $\Delta C_S$ of sulfur concentration $C_S$ should be 0.05 wt%-S.

Such resolutions of X and $C_S$ may be obtained using a density-compensated signal from measuring apparatus M in FIG. 1, wherein the effective length of the sample cell 2 of R-detector 1 is elongated, and the voltage applied to the ionization chamber is increased to increase the measuring sensitivity. For the sulfur concentration detector 7, a gamma ray source or an X-ray source of 60 to 100 keV energy is used whereby a silver-tin target (silver-to-tin area ratio: 50/50), a cadmium target or an indium target is caused to emit 23 to 24.5 keV flourescent X-rays as in the embodiment of FIG. 1. This sulfur detector, as set forth in U.S. Pat. No. 3,746,874 is capable of detecting sulfur concentrations with a sensitivity of 0.01 wt%-S by the use of 23 to 24.5 keV flourescent X-rays.

The required repeatability of an apparatus handled by one identical person, defined in JIS (Japanese Industrial Standards) K2279–1971 for the method of testing the calorific power of petroleum products, is 50 kcal/kg. Thus the resolution available according to the invention is 1/2.5 of the repeatability defined in JIS and a calorimeter of high sensitivity can be realized according to the invention.

Figure 2:
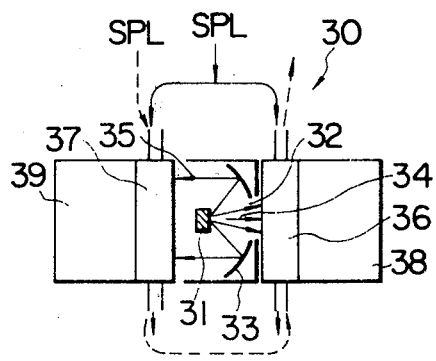
FIGS. 2 and 3 are schematic diagrams showing modified detectors for the measuring apparatus of the present invention.
Figure 3:
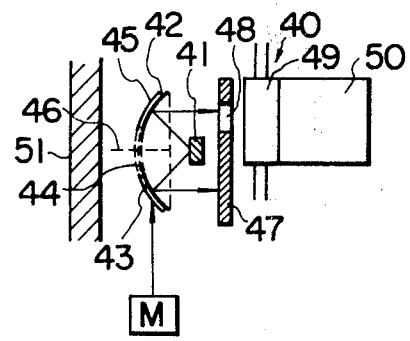

FIGS. 2 and 3 show detectors of other embodiments of the invention. The detector 30 shown in FIG. 2 comprises a radiation source 31 generating gamma rays or X-rays with an energy level, for example, of 60 keV, and a concave target 33 opposite to the radiation source 31 and having an aperture 32 in the center. This target is of silver-tin as in the foregoing example, from which gamma rays 34 are emitted with an energy level at which $\mu_H$ and $\mu_C$ differ from each other, and X-rays 35 with an energy level at which $\mu_H$ and $\mu_C$ are about equal to each other are obtained. The gamma rays are opposite in direction to the flourecent X-rays as shown in FIG. 2. Detectors such as ionization chambers 38 and 39 are located opposite the sample cells 36 and 37 in the direction in which the gamma rays and flourescent X-rays are generated. The sample SPL is branched (as indicated by the solid line) from the main sample line or is introduced directly (as indicated by the broken line) from the main sample line continuously into the sample cells 36 and 37 seriatim.

In detector 30 of FIG. 2, one radiation source and one target will suffice and hence the cost of the apparatus can be reduced, its safety can be increased, and the R-detector and the sulfur concentration detector can be integrally constructed.

The detector 40 shown in FIG. 3 comprises a radiation source 41 for generating gamma rays or X-rays with an energy level, for example, of 60 to 100 keV, and targets 42 and 43 located opposite to the radiation source 41. The target 42 is of germanium, capable of emitting flourescent X-rays of 10 keV at which $\mu_H$ and $\mu_C$ differ from each other, or of barium, capable of generating flourescent X-rays of 32 keV energy. The other target 43 is of the aforementioned silver-tin construction generating flourescent X-rays with an energy level at which $\mu_H$ and $\mu_C$ are equal to each other, or of cadmium or indium. The two targets 42 and 43 are mounted on a concave support member 45 having an aperture 44 in the center so that the two targets are suitably distant from each other to prevent flourescent X-rays with different energy levels from mixing. The support member 45 is rotated on a shaft 46 by a motor M. A shielding plate 47 is located opposite to the targets 42 and 43 and has an opening 48 alignable with one of the rotating targets 42 or 43. A sample cell 49 and a radiation detector such as an ionization chamber 50 are located on the side opposite to the target in view of the opening 48. A shielding wall 51 shields the gamma rays or X-rays escaping from the aperture 44 in the center of the support member 45.

In operation, detector 40 has its targets 42 and 43 rotated along with the support member 45 at a constant speed by the motor M. As a result, the targets 42 and 43 alternately pass a position in front of the opening 48 of the shielding plate 47. The flourescent X-rays with different energy levels generated from the targets 42 and 43 alternately pass through the opening 48 of the shielding plate 47 and enter the sample cell 49. The flourescent X-rays transmitted through the sample cell 49 are detected by the ionization chamber 50. Thus a signal which varies with the sulfur concentration $C_S$ and the ratio R of the sample, and a signal which varies not with R but with the sulfur concentration $C_S$, are alternately generated from the detector 40 as if controlled on a time-division basis. These two signals are separated from each other by a suitable signal separation circuit and then processed as in the example illustrated with reference to FIG. 1 to obtain the calorific power Q of the sample.

In detector 40 of FIG. 3, one radiation source, one sample cell, and one radiation detector are sufficient, which makes it possible to construct the entire detector into a small size and manufacture it at a lower cost.

In the above example gamma rays of 60 keV energy and X-rays of 10 to 32 keV energy are the illustrative examples used for the R-detector. Instead, other gamma rays and X-rays may be used as long as their energy levels are sufficiently distant from the value (about 20 keV) at which $\mu_H$ is equal to $\mu_C$. However, when gamma rays whose energy level is about 60 keV are used, the mass absorption coefficient of sulfur becomes small. Hence the amount of sulfur compensation is reduced and transmittance of gamma rays is increased, with the result that the thickness of the window of the sample cell can be increased.

In the foregoing examples, a computer system or element 22 may be used for the division computations eliminating the density signal as performed by division circuits 20 and 21, as well as for the arithmetic operations correlating the signal X which varies with R to the signal $C_S$ which represents sulfur concentration.

According to the invention, as has been described, gamma rays or X-rays with an energy level at which $\mu_H$ differs from $\mu_C$ are utilized, such radioactive rays are applied to a sample whereby a signal which varies with $C_S$ and R is obtained, this signal is compensated with respect to density by the density signal of the sample and then computed according to a given formula to determine the calorific power of the sample. According to the invention, therefore, the calorific power of a hydrocarbon compound can be measured continuously with high accuracy. Moreover, because the calorific power is measured through a given formula correlating the signal varying with $C_S$ and R to the signal representing sulfur concentration $C_S$, the calorific power of a sulfur-containing hydrocarbon compound such as crude oil and petroleum can be continuously measured with high accuracy.

Thus it is evident that the apparatus of this invention is highly suited for the measurement of calorific power of crude oil and petroleum products in various plants such as power plants where a large volume of crude oil or petroleum is consumed as fuel.

Although specific embodiments of the invention have been disclosed herein in detail, it is to be understood that this is for the purpose of illustrating the invention, and should not be construed as necessarily limiting the scope of the invention, since it is apparent that many changes can be made to the disclosed structure by those skilled in the art to suit particular applications.

We claim:

1. An apparatus for measuring the calorific power of a sample containing hydrocarbon compounds and sulfur, comprising:
   means for generating gamma rays or x-rays at an energy level for which the mass absorption coefficient of carbon differs from that of hydrogen;
   means for applying the gamma rays or x-rays to the sample;
   means for detecting the absorption rate of the gamma rays or x-rays by the sample and for generating a signal varying with the samle density and with the concentrations of carbon, hydrogen and sulfur in the sample;
   means for measuring the density of the sample and for generating a signal varying therewith;
   means for measuring the concentration of sulfur in the sample and for generating a signal varying therewith, said means comprising means for generating gamma rays or x-rays at an energy level for which the mass absorption coefficient of carbon is about equal to that of hydrogen, means for applying the gamma rays or x-rays to the sample, an ionization chamber for generating a signal varying exponentially with the concentration of sulfur in the sample, and linearizing circuit means receiving the exponentially varying signal and generating a signal varying linearly with the concentration of sulfur in the sample, and means for accepting the signal varying with density and the concentrations of carbon, hydrogen and sulfur, the signal varying with density, and the signal varying with sulfur concentration and for mathematically correlating said signals according to a predetermined arithmetic formula to directly obtain the calorific power of the sample.

2. An apparatus for measuring the calorific power of a sample containing hydrocarbon compounds and sulfur, comprising:

means for generating gamma rays or x-rays at an energy level for which the mass absorption coefficient of carbon differs from that of hydrogen;

means for applying the gamma rays or x-rays to the sample;

means for detecting the absorption rate of the gamma rays or x-rays by the sample and for generating a signal varying with the sample density and with the concentrations of carbon, hydrogen and sulfur in the sample, said means comprising an ionization chamber for generating a signal varying exponentially with the concentration of carbon, hydrogen and sulfur and with density, and linearizing circuit means accepting the exponentially varying signal and generating a signal varying linearly with density and with the concentrations of carbon, hydrogen and sulfur in the sample, means for measuring the density of the sample and for generating a signal varying therewith;

means for measuring the concentration of sulfur in the sample and for generating a signal varying therewith; and means for accepting the signal varying with density and the concentrations of carbon, hydrogen and sulfur, the signal varying with density, and the signal varying with sulfur concentration and for mathematically correlating said signals according to a predetermined arithmetic formula to directly obtain the calorific power of the sample.

3. An apparatus for measuring the calorific power of a sample containing hydrocarbon compounds and sulfur, comprising:

means for generating gamma rays or x-rays at an energy level for which the mass absorption coefficient of carbon differs from that of hydrogen;

means for applying the gamma rays or x-rays to the sample;

means for detecting the absorption rate of the gamma rays or x-rays by the sample and for generating a signal varying with the sample density and with the concentrations of carbon, hydrogen and sulfur in the sample;

means for measuring the density of the sample and for generating a signal varying therewith;

means for measuring the concentration of sulfur in the sample and for generating a signal varying therewith; and means for accepting the signal varying with density and the concentrations of carbon, hydrogen and sulfur, the signal varying with density, and the signal varying with sulfur concentration and for mathematically correlating said signals according to a predetermined arithmetic formula to directly obtain the calorific power of the sample, the means mathematically correlating the signals comprising means for combining (a) the signal varying with density with (b) the signal varying with density and with the concentrations of carbon, hydrogen and sulfur to provide (c) a signal varying only with the concentrations of carbon, hydrogen and sulfur, and means for combining (c) the signal varying only with the concentrations of carbon, hydrogen and sulfur with (d) the signal varying with the concentration of sulfur to obtain the calorific power of the sample.

4. An apparatus for measuring the calorific power of a sample containing hydrocarbon compounds and sulfur, comprising:

means for generating gamma rays or x-rays at an energy level for which the mass absorption coefficient of carbon differs from that of hydrogen;

means for applying the gamma rays or x-rays to the sample;

means for detecting the absorption rate of the gamma rays or x-rays by the sample and for generating a signal varying with the sample density and with the concentrations of carbon, hydrogen and sulfur in the sample;

means for measuring the density of the sample and for generating a signal varying therewith;

means for measuring the concentration of sulfur in the sample and for generating a signal varying therewith, said means comprising means for generating gamma rays or x-rays at an energy level for which the mass absorption coefficient of carbon is about equal to that of hydrogen, means for applying the gamma rays or x-rays to the sample, and means for detecting the absorption rate of the rays by the sample and for generating a signal varying with the concentration of sulfur in the sample;

the means for generating rays at an energy level for which the mass absorption coefficient of carbon differs from that of hydrogen, and the means for generating rays at an energy level for which the mass absorption coefficient of carbon is about equal to that of hydrogen, being provided by a single source of radioactive rays and target means for receiving the radioactive rays and emitting further rays, the source and target means together providing gamma rays or x-rays at said two energy levels; and means for accepting the signal varying with density and the concentrations of carbon, hydrogen and sulfur, the signal varying with density, and the signal varying with sulfur concentration and for mathematically correlating said signals according to a predetermined arithmetic formula to directly obtain the calorific power of the sample.

5. An apparatus for measuring the calorific power of a sample containing hydrocarbon compounds and sulfur as claimed in claim 4 wherein the means for applying the rays at an energy level for which the mass absorption coefficient of carbon differs from that of hydrogen to the sample comprising means for directly impinging rays from the radioactive source upon the sample, and wherein the means for applying rays at an energy level for which the mass absorption coefficient of carbon is about equal to that of hydrogen to the sample comprises means for impinging rays emitted by the target means upon the sample.

6. An apparatus for measuring the calorific power of a sample containing hydrocarbon compounds and sulfur as claimed in claim 4 wherein the target means comprises first and second portions emitting rays at different energy levels, and the means for applying rays at an energy level for which the mass absorption coefficient of carbon differs from that of hydrogen to the sample comprises means for impinging rays emitted from the first portion of the target means upon the sample, and wherein the means for applying rays at an energy level for which the mass absorption coefficient of carbon is about equal to that of hydrogen to the sample comprises means for impinging rays emitted from the second portion of the target means upon the sample.

7. An apparatus for measuring the calorific power of a sample containing hydrocarbon compounds and sulfur as claimed in claim 6 wherein the means for detecting the absorption rate of rays at an energy level for which the mass absorption coefficient of carbon differs from that of hydrogen, and the means for detecting the absorption rate of the rays at an energy level for which the mass absorption coefficient of carbon is about equal to that of hydrogen, have a common detection chamber, and wherein said first and second portions of the target means are arranged to alternately impinge emitted rays upon the detection chamber.

8. An apparatus for measuring the calorific power of a sample containing hydrocarbon compounds and sulfur, comprising:
   a radioactive source of gamma rays;
   target means for emitting flourescent x-rays upon receiving gamma rays from the gamma ray source;
   said gamma ray source and target means being arranged to furnish first gamma rays or flourescent x-rays with an energy level at which the mass absorption coefficient of carbon differs from that of hydrogen, and second flourescent x-rays at an energy level at which the mass absorption coefficient of carbon is about equal to that of hydrogen;
   means for applying said first and second rays to the sample;
   means for detecting the absorption rates of each of said first and second rays by the sample and for generating a first signal varying with density and with the concentrations of carbon, hydrogen and sulfur in the sample, and a second signal varying with density and with the concentration of sulfur in the sample;
   means for measuring the density of the sample and for generating a signal varying therewith; and
   means for receiving the signal varying with density and the concentrations of carbon, hydrogen, and sulfur in the sample, the signal varying with density in the concentration of sulfur in the sample, and the signal varying with density, and for mathematically correlating said signals according to a predetermined arithmetic formula to obtain the calorific power of the sample.

9. An apparatus for measuring the calorific power of a sample containing hydrocarbon compounds and sulfur as claimed in claim 8 wherein the means for detecting the absorption rates of said first and second rays by the sample comprises a first detector continuously receiving said first rays and a second detector continuously receiving said second rays.

10. An apparatus for measuring the calorific power of a sample containing hydrocarbon compounds and sulfur as claimed in claim 8 wherein the means for detecting the absorption rates of said first and second rays by the sample comprises a single detector arranged to alternately receive said first and second rays.

11. An apparatus for measuring the calorific power of a sample containing hydrocarbon compounds and sulfur as claimed in claim 10 wherein the target means is arranged with different areas for emitting the first and second rays, and wherein the apparatus comprises means for alternately aligning the different areas with the single detector.

* * * * *